United States Patent [19]

Elsohly et al.

[11] 4,187,076

[45] Feb. 5, 1980

[54] PARAQUAT DETECTION METHOD

[75] Inventors: Mahmoud A. Elsohly; Carlton E. Turner, both of Oxford, Mich.

[73] Assignee: The University of Mississippi, University, Mich.

[21] Appl. No.: 927,852

[22] Filed: Jul. 25, 1978

[51] Int. Cl.² .................. G01N 31/12; G01N 31/08; G01N 31/22; G01N 33/16
[52] U.S. Cl. .................. 23/230 PC; 23/230 R; 23/230 B; 23/910; 252/408
[58] Field of Search .......... 23/230 R, 230 B, 230 PC, 23/910

[56] References Cited
PUBLICATIONS

Chemical Abstracts, 83: 38344s (1975).
Chemical Abstracts, 84: 111447e (1976).

Primary Examiner—Sidney Marantz
Attorney, Agent, or Firm—William D. Stokes

[57] ABSTRACT

A method of detecting the presence of paraquat in biological tissues and fluid and soil and plant tissues, particularly marihuana, involving the conversion of any paraquat present in the tissue to 4,4'-bipyridine and analyzing the sample for that compound, the presence of which would indicate the presence of paraquat in the tissue.

31 Claims, No Drawings

PARAQUAT DETECTION METHOD

This invention relates to an improved method for the detection of paraquat in substances. The invention is particularly concerned with the detection of paraquat in biological and plant tissues and fluids. More particularly, this invention is concerned with a method for qualitatively detecting the presence of paraquat in marihuana.

Paraquat, 1,1'-dimethyl-4,4'-bipyridylium cation, which has the structural formula

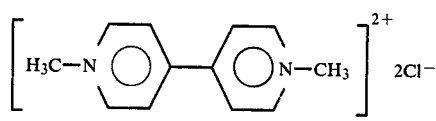

is a herbicide which exhibits a degree of selective defoliant action between weeds and crops and has residual soil action. At the time of discovery of this herbicide it was believed that it offered the possibility of revolutionary changes in agricultural techniques through the world. In some parts of the world, the herbicide is referred to as transquat. It will be understood that the active ingredient in transquat is paraquat. Since discovery, paraquat has been, and is presently, marketed on a world-wide basis. In view of its success as a defoliant in various agricultural applications, paraquat was carefully investigated and used extensively in foreign countries as an agent for chemically controlling marihuana to the desired end of reducing and eliminating the flow of illicit crude drugs from *Cannabis sativa*, hereinafter referred to as marihuana. Notwithstanding the notoriety given to the treatment of illicit fields with the toxic herbicide, illegal sale of the marihuana has not been abated. Tragically, marihuana sprayed with paraquat finds its way into the illicit trade.

It will be understood that when the marihuana is harvested subsequent to treatment with the herbicide, but prior to defoliation of the plant, the toxic material is in the plant but its presence is not readily detectable by any means heretofore known. It is estimated that not only have thirty-six million Americans experimented with marihuana, but that currently, thirteen million Americans use marihuana on a fairly regular basis. It has also been estimated that over twenty-one percent (21%) of the current street marihuana contains paraquat or transquat.

Researchers have now produced evidence of irreversible cellular damage and severe, frequently lethal, pulmonary changes indured by persons who have ingested paraquat even in small quantities. Studies have been made showing that on oral ingestion of 680$\mu$ moles/g., plasma concentration of the toxic substance remained above 5$\mu$ moles/ml. for 30 hours or more while lung concentrations exceeded a toxic threshold of 15$\mu$ moles/ml. Concentrations of the toxic chemicals in contents of the stomach and small intestine from one to sixteen hours after dosing showed a linear relationship between the plasma and intestinal concentrations of the herbicide.

A large number of tests, techniques and methods have been proposed and used for the detection of paraquat in biological and plant tissues; however, substantially all of the heretofore known methods are complicated, require skilled technicians, are relatively expensive, and require a great deal of time. In addition, quite a few of the proposed tests and methods give inaccurate and often misleading results. One of the major disadvantages of the known qualitative methods is the fact that most cannot detect the presence of paraquat below a concentration of 150 ppm. The failure and/or inaccurate results of the known tests may be attributed, in part, to the fact that the toxic chemical is absorbed into the tissue of the plant which absorbed chemical is not extracted using the known methods. All of the heretofore tests for paraquat have depended upon the detection of paraquat per se.

Tests for the determination of paraquat are described in the following publications:
1. Spectrophotometric Determination of Diquat and Paraquat in Aqueous Herbicide Formulations, S. H. Yuen, J. E. Bazness and D. Nyles, Analyst, Lond., 1967 92, 375–381.
2. An Ion-Exchange Method for Determining Paraquat Residues in Food Crops, Calderbank and Yuen, Analyst 1965,99–106.
3. Collaborative Check for Paraquat in Formulations, Carlstrom (Chevron Chemical Co.) J. Ass. Off. Analyt. Chem., 1971, 54 (3), 718–719.
4. Chromatographic Parameters of the Bisquaternary Herbicides Paraquat and Diquat, Sharp and Lores, J. Aric. Fed. Chem., 1974, 22 (3) 458–461.
5. Determination of Paraquat (1,1'-dimethyl-4,4'-bipyridylium cation) in Urine, Berry and Grove, Clinica Chim. Acta, 1971, 34 (1), 5–11.
6. Chevron Chemical Company's Method of Analysis of Paraquat Residues, published July 28, 1976.

While there was a recognized and urgent need for a simple, practical and accurate test for the determination of the presence of paraquat in biological tissue and fluid, soil and plant tissues, there was a particularly urgent need for a simple, practical and accurate test for the detection of the presence of paraquat in marihuana which could be carried out by persons having the minimum of skills in the art.

In accordance with this invention, there is provided a simple, practical, reproducible and relatively inexpensive method for detecting the presence of paraquat in biological tissues, fluids, plant tissues, and soil, particularly marihuana in concentrations as low as 1.0 ppm. One of the major advantages of the present inventive method is that it utilizes readily available chemicals and equipment and may be carried out by persons with the minimum of skills in the art. That the invention presents a major advance in the art will be recognized from the description hereinafter.

Broadly, the method of the invention is a colorimetric method for the detection of paraquat in body and plant tissue and fluids. Even though the method of the invention does not depend upon the analysis of paraquat per se, it provides the advantage of relatively fast and accurate test for the presence of extremely small quantities of the chemical. The invention is specifically based on the discovery that paraquat in biological tissue and fluids, soils, and plant tissues is readily converted to 4,4'-bipyridine upon heating to a relatively high temperature, e.g. about 300 degrees C., and that the compound, if present, is easily extracted and its presence detected by simple chromatographic means. In actual practice, any 4,4'-bipyridine present in the test sample is trapped as its salt by the addition of a relatively non-volatile mineral acid, for example, sulfuric acid and phosphoric acid. The 4,4'-bipyridine salt formed is then converted to 4,4'-bipyridine, extracted out, and its presence detected by simple chromatographic means. The amount of 4,4'-bipyridine present is directly proportional to the amount of paraquat originally in the specimen. The general reaction is as follows:

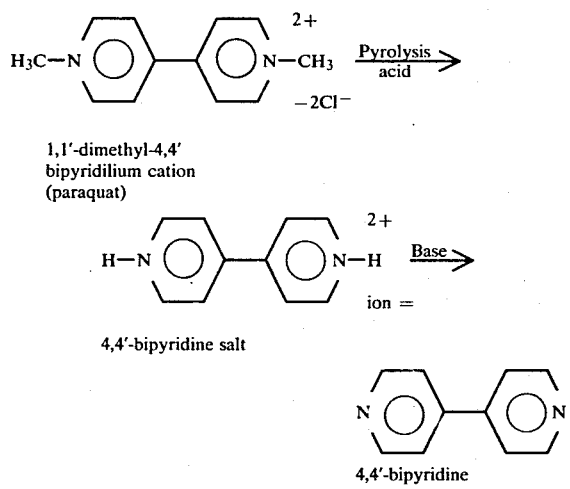

1,1'-dimethyl-4,4' bipyridilium cation (paraquat)

4,4'-bipyridine salt 4,4'-bipyridine

When paraquat is pyrolyzed with a non-volatile mineral acid, 4,4'-bipyridine salt is formed. The salt is extracted from the pyrolyzed product and converted to a 4,4'-bipyridine by treating the extraction product with a base. Relatively pure 4,4'-bipyridine is then extracted by any water immiscible organic solvent for the chemical. Any bipyridine present is then readily detected by any one of many chromatographic techniques. In the preferred embodiment, for accuracy, simplicity and speed, paper chromatography has been found to be advantageous.

Other chromatographic techniques useful in the process of the invention may be, for example, thin layer chromatography, gas chromatography and gas chromatography using nitrogen and flame ionization detectors. It was discovered that using paper chromatographic techniques, the solvent system gave a good $R_f$ value and could be used without impregnation of the paper prior to use. While numerous solvents could be used it was discovered that plain water met all of the criteria, i.e., developed 4,4'-bipyridine, gave an $R_f$ of 0.5, is readily available, economical and gives dependable results.

As will be appreciated by those skilled in the art, various chromogens or color forming materials or color indicators are known for the detection of pyridilium compounds, however, the color reagent used in the process of the invention are preferably iodoplatinate which gives a blueish-green color with 4,4'-bipyridine, or Dragendorff's reagent which gives an orange-red color with 4,4'-bipyridine. While Dragendorff's reagent is, perhaps, not as sensitive as iodoplatinate, it is the preferred reagent because of its ready availability, relative cheapness, and capability of accurately developing 4,4'-bipyridine in amounts as low as 0.05–0.1 μg.

As previously mentioned, the extracting agent for 4,4'-bipyridine may be any organic solvent for the chemical which is immiscible with water, for example, benzene, toluene, ether, chloroform and ethyl acetate. In the preferred embodiment, ethyl acetate is used. All of the color agents useful in the process of the invention are readily known and available in the trade. A modified Dragendorff's color reagent can be advantageously used and may be quickly prepared as follows:

1. Solution A: Dissolve 1.7 g bismuth subnitrate in 100 ml of a water acetic acid mixture (80:20);
2. Solution B: Dissolve 40 g potassium iodide in 100 ml water;
3. Mix 5 ml each of Solutions A and B together with 20 ml acetic acid and 70 ml of water.

While different types of chromatographic paper may be found suitable for the paper chromatography used in the process of the invention, Whatman No. 3 MM chromatographic paper is preferred. The range of concentration of the various reagents used in the detecting method of the invention are not critical, however, certain guidelines may be established in this regard. It is desirable to keep the volume of reagents used to a minimum for the reason that the detectable amount of paraquat which might be present is quite small with respect to the size of the sample. Moreover, since evaporation and drying steps are used in the process, small quantities of reagents are advantageous. On the other hand, dilute acids and bases are used for the reason that the more concentrated acids and bases offer an inherent danger to the user. The concentration of acid used in the method of the invention is advatageously and preferably for the foregoing reasons, in the range of about five percent to fifty percent (5.0%–50.0%). Ten percent (10%) by volume acid has been found quite advantageous. The basifying agent used is preferably dilute sodium hydroxide having a concentration of about twenty-five percent (25%) by volume. It will be understood that other bases, e.g., ammonium hydroxide, sodium carbonate, potassium hydroxide, potassium carbonate, to name a few, may be used as the basifying agent. It will also be readily understood that the concentrations of the base selected is also a matter of choice of the user. It will be appreciated from the specific examples hereafter that the criteria for selection of concentration of the acids and bases used is solely one of convenience, particularly ease of handling and working with small volumes to expedite evaporation when required.

The detection system of the invention may be provided in kit form for simple and relatively fast detection of the presence of 4,4'-bipyridine, hence paraquat.

The followng examples will illustrate the improved detection method of the invention.

EXAMPLE 1

Illicit marihuana confiscated by the Drug Enforcement Administration (DEA) was used in the examples of the invention. Samples of confiscated marihuana were tested for paraquat concentration using the Chevron Chemical Company's method of analysis of paraquat residues published July 28, 1976. Batches of marihuana containing respectively 11.0 ppm paraquat, 49.8 ppm paraquat, 101 ppm paraquat, and 225 ppm paraquat were found in the confiscated material. Samples containing 1.0 ppm paraquat were prepared by intimately mixing 0.2 g of ground marihuana containing no paraquat. Marihuana containing no paraquat was used as a control in all tests. The marihuana samples were finely ground to a powder prior to testing. The various samples were numbered and coded in such a manner that the person carrying out the analysis of the invention did not know initially whether there was any paraquat present in the sample tested, nor the concentration of paraquat, if any, in the sample being tested. Subsequent to all of the tests, the results were correlated with the test code samples.

EXAMPLES 2–6

A minimum of ten one gram samples from each batch of ground marihuana prepared in accordance with Example 1 having respectively 1.0 ppm, 11.0 ppm, 49.8 ppm, 101 ppm and 25 ppm paraquat and control samples were placed in beakers. Two (2) ml 10% sulfuric acid was then added to each sample with stirring and allowed to stand for a few minutes. Each beaker was then placed on a hot plate and heated with continuous stirring of the sulfuric acid-marihuana mixture until all of the material was completely charred. If there is complete charring, no smoke will be given off. It is essential for optimum results that all of the samples be completely charred. That the material has been properly charred will also be evidenced by a clear filtrate upon subsequent dilution and filtration. During the charring step any paraquat present will be converted to 4,4'-bipyridinedisulfate. The charred material was cooled in the beaker to room temperature. Three (3) ml of 10% sulfuric acid was then added to each of the charred samples and heated to boiling with stirring. Each sample was slightly cooled and diluted with three (3) ml water. The material was then filtered through cotton plugs into test tubes. Each of the beakers were also washed with an additional three (3) ml water to insure collection of all of the chemical. Each wash water was also filtered through the respective cotton filter. Two (2) ml 25% sodium hydroxide was added to each filtrate with stirring thereby converting any 4,4'-bipyridinedisulfate present to 4,4'-bipyridine. After cooling to room temperature two (2) ml of ethyl acetate was added to each of the basified solutions and vigorously agitated and allowed to separate into two layers. The organic (upper) layers containing any 4,4'-bipyridine present were transferred to small test tubes and evaporated to dryness. The evaporated residues were reconstituted with one-two drops of ethyl acetate. It will be understood that the organic solution may also be evaporated to a volume of one-two drops eliminating thereby the evaporation step.

The reconstituted solutions were spotted about one inch from the end of strips of Whatman No. 3 MM filter paper. The ends of the strips were then immersed in water which was allowed to wick up the paper for a distance of about three inches. To expedite drying, the strips were held in a gently moving stream of warm air. The dried strips were then immersed in Dragendorff's solution and removed. All of the strips having samples which originally contained paraquat developed a dark reddish-orange spot approxiately two inches above the bottom of the strip. No spots developed in the samples which did not initially contain paraquat.

All of the tests of Examples 2–6 were repeated using thin layer chromatographic techniques on plates of silica gel G. Iodoplatinate, as well as Dragendorff's solution, was also used as a color developer giving excellent results. Varying the concentrations of sulfuric acid and sodium hydroxide had little or no effect on the accuracy of the tests. Similar tests to those of Examples 2–6 were also carried out using other non-volatile mineral acids in addition to sulfuric acid, e.g., phosphoric acid and other basifying reagents than sodium hydroxide, e.g., ammonium hydroxide, potassium hydroxide, and sodium carbonate and the detection system gave extremely accurate results.

It will be clearly understood by those skilled in the art that certain changes may be made in the above compositions and methods. It is therefore intended that all matter contained in the foregoing description shall be interpreted as illustrative and not in a limited sense. It is also understood that other modifications may be made without departing from the spirit and scope of the instant invention.

What is claimed is:

1. The process for detecting the presence of paraquat in a material comprising the steps of converting any paraquat present in the material to a pyrolysis stable salt of 4,4'-bipyridine, converting any said 4,4'-bipyridine salt present to 4,4'-bipyridine and analyzing said sample for the presence of 4,4'-bipyridine, the presence of which indicates the presence of paraquat in the material.

2. The process of claim 1 wherein the presence of 4,4'-bipyridine is determined by chromatographic analysis.

3. The process of claim 2 wherein the chromatographic method of analysis is paper chromatography using a chromatographic reagent selected from the group consisting of iodoplatinate and Dragendorff's solution.

4. The process of claim 2 wherein the chromatographic method of analysis is thin layer chromatography using a chromatographic reagent selected from the group consisting of iodoplatinate and Dragendorff's solution.

5. The process of claim 1 wherein any paraquat present in the material is converted to the 4,4'-bipyridine salt by a process comprising the steps of grinding the material, adding a non-volatile mineral acid to the ground material with stirring; and applying sufficient heat to the acid treated material to char the mixture.

6. The process of claim 5 wherein the non-volatile mineral acid is a 10% sulfuric acid.

7. The process of claim 5 wherein the non-volatile mineral acid is selected from the group consisting of sulfuric acid and phosphoric acid.

8. The process of claim 7 wherein the non-volatile mineral acid has a concentration in the range of about 5% to 50% by volume.

9. The process of claim 5 wherein any 4,4'-bipyridine salt present in the material is converted to 4,4'-bipyridine by the addition of a base in a basifying quantity.

10. The process of claim 9 wherein the base is selected from the group consisting of sodium hydroxide, sodium carbonate, potassium hydroxide and potassium carbonate.

11. The process of claim 10 wherein the base used is a 25% solution of sodium hydroxide.

12. The process for detection of paraquat in a material comprising the steps of converting any paraquat present in the material to 4,4'-bipyridinedisulfate, converting any said 4,4'-bipyridinedisulfate present to 4,4'-bipyridine and analyzing said sample for the presence of 4,4'-bipyridine, the presence of which indicates the presence of paraquat in the material.

13. The process of claim 12 wherein any paraquat present in the material is converted to 4,4'-bipyridine disulfate by the steps comprising grinding the material, adding sulfuric acid to the ground material with stirring and applying sufficient heat to the acid treated material to char the mixture.

14. The process of claim 12 wherein the non-volatile acid has a concentration in the range of about 5% to 50%.

15. The process of claim 12 wherein the presence of 4,4'-bipyridine is determined by chromatographic analysis.

16. The process of claim 12 wherein any 4,4'-bipyridinedisulfate present in the sample is converted to 4,4'-bipyridine by the addition of dilute sodium hydroxide to the sample in a basifyng quantity.

17. The process of claim 16 wherein the chromatographic method of analysis is paper chromatography using a chromatographic agent selected from the group consisting of iodoplatinate and Dragendorff's solution.

18. The process of claim 16 wherein the chromatographic method of analysis is thin layer chromatography using a chromatographic reagent selected from the group consisting of iodoplatinate and Dragendorff's solution.

19. The process for the detection of paraquat which may be present in plant tissue comprising the steps of adding a non-volatile mineral acid to the plant tissue with stirring, charring the acid-tissue mixture by applying heat thereto, whereby any paraquat present is converted to 4,4'-bipyridine salt; extracting any 4,4'-bipyridine salt present with a solvent for the compound; basifying the sample with a base whereby any 4,4'-bipyridine salt is converted to 4,4'-bipyridine; extracting any 4,4'-bipyridine present with an organic water immiscible solvent for the compound; and chromatographically analyzing the organic solution for the presence of 4,4'-bipyridine whereby the presence of 4,4'-bipyridine indicates the presence of paraquat in the plant tissue.

20. The process of claim 19 wherein the acid is sulfuric acid.

21. The process of claim 19 wherein the acid is phosphoric acid.

22. The process for the detection of paraquat in marihuana comprising the steps of intimately mixing the plant tissue with sulfuric acid; applying sufficient heat to completely char the sulfuric acid-marihuana mixture whereby any paraquat in the tissue is converted to 4,4'-bipyridinedisulfate; extracting any 4,4'-bipyridinedisulfate present with sulfuric acid; basifying the solution containing 4,4'-bipyridinedisulfate with sodium hydroxide whereby any 4,4'-bipyridinedisulfate present is converted to 4,4'-bipyridine; extracting any 4,4'-bipyridine present with an organic water immiscible solvent for 4,4'-bipyridine; removing the organic solvent layer; evaporating the organic solvent to about one to two drops; and chromatograpically determining the presence of 4,4'-bipyridine which indicates presence of paraquat in the marihuana.

23. The process of claim 22 wherein the dilute sulfuric acid has a concentration in the range of about 5% to 50% by volume.

24. The process of claim 22 wherein the sodium hydroxide has a concentration of about 25% by volume.

25. The process of claim 22 wherein the organic solvent for 4,4'-bipyridine is selected from the group consisting of ethyl acetate, toluene, ether, benzene and chloroform.

26. The process of claim 22 in which paper chromatography is used to determine the presence of 4,4'-bipyridine in the test solution and wherein water is used as the solvent system and Dragendorff's solution is used as the color agent.

27. The process for the detection of paraquat in marihuana comprising the steps of intimately mixing the plant tissue with phosphoric acid; applying sufficient heat to completely char the sulfuric acid-marihuana mixture whereby any paraquat in the tissue is converted to 4,4'-bipyridinediphosphate; extracting any 4,4'-bipyridinediphosphate present with phosphoric acid; basifying the solution containing 4,4'-bipyridinediphosphate with sodium hydroxide whereby any 4,4'-bipyridinediphosphate present is converted to 4,4'-bipyridine; extracting any 4,4'-bipyridine present with an organic water immiscible solvent for 4,4'-bipyridine; removing the organic solvent layer; evaporating the organic solvent to about one to two drops; and chromatographically determining the presence of 4,4'-bipyridine which indicates presence of paraquat in the marihuana.

28. The proces of claim 27 wherein the phosphoric acid has a concentration in the range of about 5% to 50% by volume.

29. The process of claim 27 wherein the sodium hydroxide has a concentration of about 25% by volume.

30. The process of claim 27 wherein the organic solvent for 4,4'-bipyridine is selected from the group consisting of ethyl acetate, toluene, ether, benzene and chloroform.

31. The process of claim 27 in which paper chromatography is used to determine the presence of 4,4'-bipyridine in the test solution and wherein water is used as the solvent system and Dragendorff's solution is used as the color reagent.

* * * * *

UNITED STATES PATENT OFFICE
CERTIFICATE OF CORRECTION

Patent No. 4,187,076      Dated Feb. 5, 1980

Inventor(s) Mahmoud A. Elsohly & Carlton E. Turner

It is certified that error appears in the above-identified patent and that said Letters Patent are hereby corrected as shown below:

ON THE COVER PAGE:

Change the state of residence of the inventors and the assignee from "Mich." to -- Mississippi --.

Signed and Sealed this

Twentieth Day of May 1980

[SEAL]

Attest:

SIDNEY A. DIAMOND

Attesting Officer      Commissioner of Patents and Trademarks